United States Patent [19]

Coke et al.

[11] Plant 4,926

[45] Nov. 9, 1982

[54] APPLE TREE

[75] Inventors: Stephen M. Coke; Leon I. Smith, both of Yakima, Wash.

[73] Assignees: McCormick's Fruit Tree Co. Inc., Yakima, Wash.; Bountiful Ridge Nurseries, Inc., Princess Anne, Md. ; a part interest

[21] Appl. No.: 232,507

[22] Filed: Feb. 9, 1981

[51] Int. Cl.[3] ..... A01H 5/03

[52] U.S. Cl. ..... Plt./34

[58] Field of Search ..... Plt./34

*Primary Examiner*—Robert E. Bagwill

*Attorney, Agent, or Firm*—Frank B. Robb

[57] ABSTRACT

A variety of apple of the Delicious strain which has dwarf characteristics, with wide angle branching, blooming as much as two weeks later than the "Starking" (unpatented variety), producing small, sweet, red apples similar to "Starking", and providing a root stock which supports ready grafting of pears for growing same to eliminate pear decline and other disorders of pear rootstocks to which this rootstock is not susceptible.

3 Drawing Figures

The present invention relates to a new and distinct variety of apple tree, discovered by us in the cultivated orchard of Stephen M. Coke, one of the discoverers herein, as a bud mutation on a "Starking" (unpatented) tree stump which had been pushed out.

During the period of initial observation it was noted that the bud mutation grew very slowly and budded only after other apple trees in the orchard were through with their bloom period, approximately two weeks later in fact.

Ultimately some late blooms appeared on a nearby Rose Red and our new variety which we denominate 2366C67 and which will be known commercially as "Super Clone", to thereby pollinate the blooms of our new variety producing small apples resembling crab apples in size and "Starking" Delicious in flavor. The apples had the usual light pinkish red blush and yellowish green backside with reddish stripes that characterized the "Starking".

We have asexually reproduced our new variety by grafting and the progeny resulting therefrom together with continued observation and tests of the original bud mutation, over a period of time, have conclusively demonstrated that it is definitely a new and distinct variety which has a number of distinct characteristics which distinguish it from the "Starking" variety as well as from other varieties of which we are aware:

1. Grows like a miniature apple tree with wide angles of branching the first year in contrast to only leaf growth which is usual in apple trees.

2. The dwarfing characteristics are decidedly pronounced as evidenced by the fact that seedlings after being cut back leaving five inches of stem and grafted to several pear varieties retained the dwarfing characteristics.

3. We have found that the late blooming apple and pear grafts with interstems of our new variety will delay the bloom of apples sixteen (16) days and of pears, fifteen (15) days.

4. Even though the bloom is delayed the fruit matures at just about the normal time.

5. Use of our new variety as a clonal rootstock will dwarf in size both apple and pear cultivars.

6. The use of our new variety as a rootstock for pears has been found to eliminate pear decline and other disorders associated with pear rootstock since apple roots are immune to these disorders.

7. The delayed blooming of our new apple variety will save substantially by delaying the time when orchard heating might be necessary, since the blooming two weeks later than usual and other known varieties takes place.

8. The dwarf characteristics and small, sweet apples produced provide a novelty item for home gardeners and make possible growing several varieties of apples and pears on the same tree.

The accompanying drawing shows a typical tree of our new variety, typical specimens of the fruit, and one specimen shown in cross-section, all as depicted in color as nearly true as it is reasonably possible to make the same in a color illustration of this character.

There follows a detailed description of our new variety, with color terminology in accordance with the Nickerson Color Fan, published by Munsell Color Company and being indicated, except where general color terms of ordinary dictionary significance are applicable:

Locality where grown and observed: At Yakima, Wash. and in the orchard of one of the discoverers hereof and in Princess Anne, Md. at Bountiful Ridge Nurseries.

Date of first and last picking: All picked by October 15.

Tree: Small (dwarf). Medium vigorous; upright; low; dense; round; slow growing; hardy; productive; regular bearer.

*Truck.*—Medium; smooth.

*Branches.*—Medium; smooth; much branching; color — Brown to green (2.5Y 4/4 moderate olive brown). Lenticels — Few; small.

*Leaves.*—Length — 3 2/10". Width — 1 5/10". Small; narrow; long; oval; taper-pointed; medium thickness; color — Medium green (7.5GY 4/4 moderate olive green) smooth. Margin — Crenate; finely serrate. Petiole — Length 1 4/10"; medium; slender.

*Flowers.*—Self-unfruitful but profusely blooming. Dates of first and full bloom — May 8 and May 13. Late compared with other varieties, 16 days later than Rose Red Delicious. (U.S. Plant Pat. No. 3,485) Medium size; white.

Fruit:

*Maturity when described eating hard.*—October 15.

*Size.*—Axial diameter 2 1/10"; transverse 1 9/10".

*Form.*—Uniform; symmetrical; regular; oblate.

*Cavity.*—Symmetrical; acute. Depth 4/10"; breadth 3/10".

*Basin.*—Rounded; base wide; pubescent.

*Stem.*—Clubbed; stout. Length 5/10". Bracts present (2).

*Calyx.*—Closed; segments persistent. Broadly; acuminate; length 5/10"; erect; pubescent; (both outer and inner surface).

*Eye.*—Small; partially closed.

*Skin.*—Thin; tough; smooth; glossy; waxed; wanting; small; even; circular; color of dots white; distribution of dots scattered; ground color 10Y8/11 strong greenish yellow. Color markings — Striped; bright. Bloom — Wanting. General color effect — Deep pink 2.5R6/11.

Flesh: Juicy; color of flesh white with yellowish tint.

*Texture.*—Firm; fine; crisp.

*Flavor.*—Mild; sweet; delicate; aroma is distant. Quality — good. Resembles Starking Delicious.

Core:

*Sessile.*—Bundle area (longitudinal section) medium; ovate; symmetrical; halves of area — equal. Bundles — green; inconspicuous; one whorl. Alternate bundle — reaches tube at below stamen. Core lines clasping — meeting; in cross-section distinct; carpellary area distinct; small.

*Calyx.*—Pubescent; apex narrowly, cone-shaped. Stem of funnel short. Depth of tube to shoulder 4/10". Entire depth 5/10". Styles — Present; distinct; base; pubescent.

*Stamens.*—One; distinct; median.

*Axillary cavity.*—Wanting.

*Seed cells axile.*—Closed. Cell walls approximate; thin; tough; length 4/10"; breadth 2/10". Longitudinal section — narrowly ovate; oblong; acute. Surface entire — smooth. Cross section — broad.

Seeds: Number perfect 10; Imperfect 0. Largest number in one cell 2. Length 3.5/10th inch. Breadth 2/10".

*Form.*—Acuminate.

*Color.*—10YR4/4 Moderate yellowish brown.

Use: Dessert; fruit is of no commercial value.

Keeping quality: Medium.

Resistance to:

*Insects.*—Good.

*Diseases.*—Good.

We claim:

1. A new and distinct variety of apple tree, substantially as herein shown and described, characterized particularly as to novelty by the unique combination of a dwarf resemblance to "Starking" (unpatented) Delicious, the fruit being similarly dwarf on the order of a crab apple, though having coloring resembling "Starking", the wide angle branching habit the first year as opposed to the usual mostly leafy growth of most apple varieties, late blooming, as much as sixteen days later than Rose Red, Jonathan and other similar varieties, and the very suitable use as a clonal rootstock for other apple varieties and also many pear varieties which when grown on usual pear rootstock are susceptible to pear decline and other pear disorders, to which the apple rootstock of this variety is not susceptible.

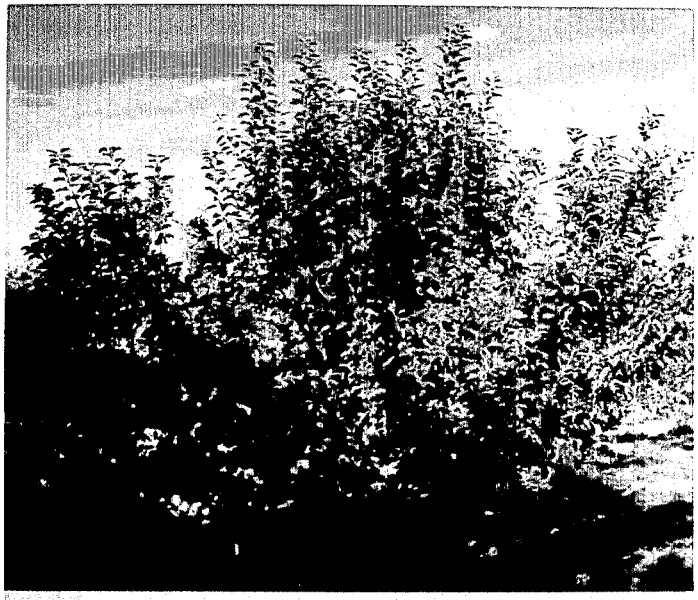
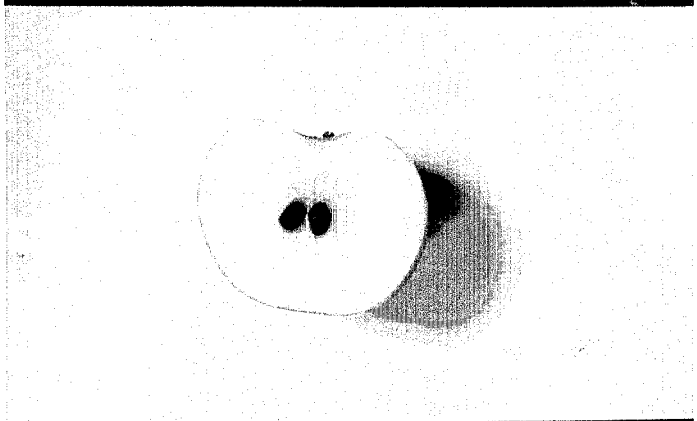
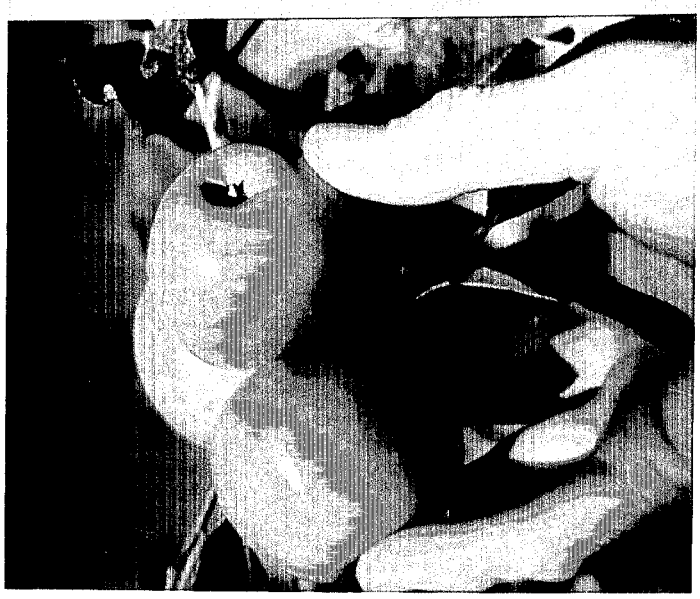

* * * * *